United States Patent
Saha

(10) Patent No.: US 7,939,308 B2
(45) Date of Patent: May 10, 2011

(54) BIO-BASED METHOD FOR MAKING MANNITOL

(75) Inventor: Badal C. Saha, Peoria, IL (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 799 days.

(21) Appl. No.: 11/973,997

(22) Filed: Sep. 25, 2007

(65) Prior Publication Data

US 2009/0023195 A1    Jan. 22, 2009

Related U.S. Application Data

(62) Division of application No. 11/006,800, filed on Dec. 7, 2004, now abandoned, which is a division of application No. PCT/US03/15568, filed on May 15, 2003, and a division of application No. 10/146,616, filed on May 15, 2002, now Pat. No. 6,855,526.

(51) Int. Cl.
*C12N 9/04*      (2006.01)

(52) U.S. Cl. ............... 435/190; 435/252.9; 424/94.1

(58) Field of Classification Search ............... None
See application file for complete search history.

(56) References Cited

OTHER PUBLICATIONS

Korakli et al., FEMS Microbiology Letters 220 (Mar. 6, 2003) 281-286.*
Martinez et al., J. of Biological Chemistry, 1963, vol. 238, pp. 1598-1603.*
Mills et al., Letters in Applied Microbiology 1990,11,211-213.*

\* cited by examiner

*Primary Examiner* — Irene Marx
(74) *Attorney, Agent, or Firm* — John Fado; Randall E. Deck; Lesley Shaw

(57) ABSTRACT

Mannitol is produced in a highly efficient fermentative method using *Lactobacillus intermedius* NRRL B-30560, or in a biochemical method using mannitol dehydrogenase isolated from this strain. Fructose serves as the primary carbon substrate in both the fermentative and biochemical conversions, but important secondary carbon sources include glucose, maltose, mannose and galactose. Mannitol is useful in the food, pharmaceutical, and medicine industries as a sweet-tasting bodying and texturing agent.

1 Claim, 3 Drawing Sheets

SEQUENCE LISTING

```
<160> NUMBER OF SEQ ID NOS: 1

<210> SEQ ID NO 1
<211> LENGTH: 20
<212> TYPE: PRT
<213> ORGANISM: Lactobacillus intermedius

<400> SEQUENCE: 1

Met Lys Ala Leu Val Leu Gln Gly Ile Lys Asp Leu Ala Val Gln Asp
  1               5                  10                  15

Tyr Glu Val Pro
            20
```

BIO-BASED METHOD FOR MAKING MANNITOL

CROSS-REFERENCE TO RELATED APPLICATION

The invention is a division of application Ser. No. 11/006,800, filed Dec. 7, 2004, which is a division of application Ser. No. 10/146,616, filed May 15, 2002, and PCT Application No. PCT/US03/15568, filed on May 15, 2003, both of which are herein incorporated by reference herein.

BACKGROUND OF THE INVENTION

1. Field of the Invention

This invention relates to a fermentation method for the production of mannitol and to a mannitol dehydrogenase useful for producing mannitol from a variety of readily available carbohydrate substrates, especially fructose and glucose.

2. Description of the Prior Art

Mannitol, a naturally occurring polyol, is widely used in the food, pharmaceutical, medicine and chemical industries (Soetaert et al., *Agro Food Ind. Hi-Tech.* 6:41-44, 1995). It is used as a sweet-tasting bodying and texturing agent. Mannitol reduces the crystallization tendency of sugars and is used as such to increase the shelf-life of foodstuffs. Crystalline mannitol exhibits a very low hygroscopicity, making it useful in products that are stable at high humidity. It is extensively used in chewing gum. Because of its desirable properties, mannitol is commonly used in the pharmaceutical formulation of chewable tablets and granulated powders. It prevents moisture absorption from the air, exhibits excellent mechanical compressing properties, does not interact with the active components, and its sweet cool taste masks the unpleasant taste of many drugs (Debord et al., *Drug Dev. Ind. Pharm.* 13:1533-1546, 1987). The complex of boric acid with mannitol is used in the production of dry electrolytic capacitors. It is an extensively used polyol for production of resins and surfactants. Mannitol is used in medicine as a powerful osmotic diuretic and in many types of surgery for the prevention of kidney failure and to reduce dye and brain oedema. Mannitol hexanitrate is a well known vasodilator, used in the treatment of hypertension.

Mannitol is currently produced industrially by high pressure hydrogenation of fructose/glucose mixtures in aqueous solution at high temperature (120-160° C.) with Raney nickel as catalyst. Typically, the hydrogenation of a 50/50 fructose/glucose mixture results in an approximately 30/70 mixture of mannitol and sorbitol (Makkee et al., *Starch/Starke* 37:136-141, 1985). Therefore about half of the fructose is converted to mannitol and half of it to sorbitol. The glucose is hydrogenated exclusively to sorbitol. As a consequence, the commercial production of mannitol is always accompanied by the production of sorbitol, thus reducing the conversion efficiency of substrate to mannitol (Soetaert et al., 1995, supra).

In recent years, research efforts have been directed towards production of polyols by fermentation and enzymatic means (Vandamme et al. *FEMS Microbiol. Rev.* 16:163-186, 1995). Yun et al., (*Biotechnol. Letts.* 18:35-40, 1996) describe microbial transformation of fructose to mannitol by *Lactobacillus* sp. KY-107. In shake flask cultures, Yun et al. obtained a final concentration of 70 g mannitol/L from 100 g D-fructose within 80 h at 28° C. Yun et al. (*J. Ferment. Bioeng.* 85:203-208, 1998) report the isolation of two mannitol-producing, lactic acid bacteria from kimichi, a traditional Korean food. *Lactobacillus* sp. Y-107 transformed fructose to mannitol from the early growth stage, with a 54% conversion yield after 20 h; whereas *Leuconostoc* sp. Y-002 converted fructose to mannitol more slowly with a 40% yield at 20 h. Yun et al. (1998, supra) describe the pathway for microbial mannitol formation as comprising two mechanisms. In the first mechanism, NADPH-linked mannitol dehydrogenase directs the reduction of fructose. In the second mechanism, fructose-6-phosphate is initially reduced to mannitol-1-phosphate by means of NAD(P)H-linked mannitol-1-phosphate dehydrogenase. The mannitol-1-phosphate is then converted to inorganic phosphate and mannitol by means of a specific mannitol-1-phosphatase.

Korakli et al. (*Adv. Food Sci.* (CTML) 22:1-4, 2000) describe the production of mannitol in a fermentation process with selected strains of *Lactobacillus sanfranciscensis* with the ability to utilize maltose, sucrose and glucose as carbon sources. Cells of strain LTH 2590 were adapted to sucrose, but gave a decreased yield of mannitol production in relation to the fructose content of sucrose.

Itoh et al. (European Patent Number EP0486024, 1992) teaches the use of *Lactobacillus* sp. B001 (FERM BP-3158) for the production of mannitol, acetic acid and lactic acid on carbohydrate substrates comprising glucose and fructose. Itoh et al. reports obtaining a level of 12.3% mannitol in 23 h with a yield of sugar of 61%. Though being able of use other sugars, such as glucose, galactose, maltose and xylose, strain B001 does not metabolize mannose or trehalose.

SUMMARY OF THE INVENTION

I have now discovered a highly efficient fermentative method for the production of mannitol using a strain of *Lactobacillus intermedius*, as well as a biochemical method using mannitol dehydrogenase isolated from the *L. intermedius* strain. Fructose serves as the primary carbon substrate in both the fermentative and biochemical conversions, but important secondary carbon sources include glucose, maltose, mannose, raffinose and galactose.

In accordance with this discovery, it is an object of the invention to provide a fermentative method for production of mannitol.

It is also an object of the invention to introduce a heretofore unrecognized bacterial source for use in efficient conversion of fructose and other carbon sources to mannitol.

Another object of the invention is to provide microbiological and biochemical alternatives to chemical production of mannitol.

Yet another object of this invention is to provide a microbial source of mannitol for use in foods and pharmaceuticals.

A further object of the invention is to provide a novel mannitol dehydrogenase isolated from *L. intermedius* for use in the biochemical conversion of fructose substrates to mannitol.

Other objects and advantages of the invention will become apparent from the ensuing description.

DEPOSIT OF BIOLOGICAL MATERIAL

Figure 1:
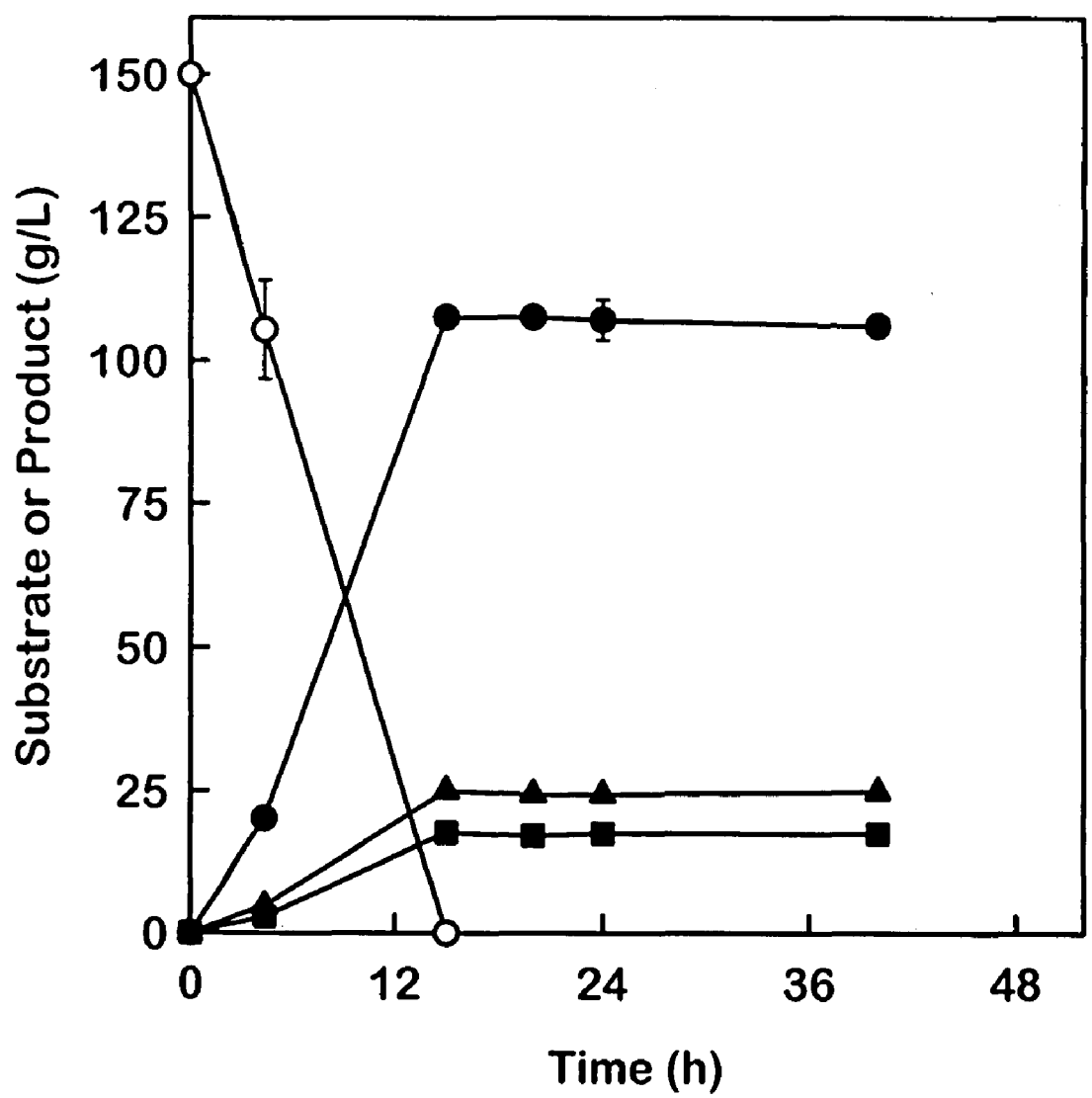
FIG. 1 is a time course of fructose (150 g/L) utilization and mannitol production by *Lactobacillus intermedius* B-30560 in pH-controlled batch fermentation at 35° C. Symbols: ○, Fructose; ●, Mannitol; ▲, Lactic acid; ■, Acetic acid.

*Lactobacillus intermedius* B-3693 described herein was redeposited on Mar. 4, 2002, under the provisions of the Budapest Treaty in the Agricultural Research Culture Collection (NRRL) in Peoria, Ill., and has been assigned Accession number NRRL B-30560. Hereafter, the *L. intermedius* for use in the invention will be referred to by the B-30560 Accession number.

DETAILED DESCRIPTION OF THE INVENTION

The primary carbon source for use in the method of the invention is fructose, which may in fact be used as the sole carbon source. Secondary carbon sources for use in combination with fructose are glucose, maltose, mannose, raffinose and galactose, without limitation thereto. Unlike *Lactobacillus* sp. B001, *L. intermedius* B-30560 can utilize trehalose very well, but cannot utilize xylose at all. Starch is also useful as a secondary carbon source, provided that glucoamylase is introduced into the fermentation medium to promote saccharification during the course of the fermentation. The amount of secondary carbon source can be up to about 33% (w/w) of the total substrate, though it is preferred that the secondary carbon source constitute less about 25% of the carbon substrate. The secondary carbon source of choice is glucose.

The specific fermentation medium for use in the mannitol production is not necessarily critical, and selection thereof would be within the skill of an ordinary person in the art. A suitable medium would contain sources of protein, amino acids, salts and other growth stimulating components. Exemplary media would be simplified MRS medium [10 g peptone, 5 g yeast extract, 2 g ammonium citrate, 5 g sodium acetate, 0.1 g magnesium sulfate, 0.05 g manganese sulfate and 2 g disodium phosphate per liter (final pH 6.5)] and enriched MRS medium (same as the simplified medium but additionally containing 10 g beef extract and 1.0 ml Tween 80). Sodium acetate may be omitted from the simplified MRS medium. Also, peptone and yeast extract may be replaced with corn steep liquor.

Fermentations may be conducted by combining the carbon source with the medium in any suitable fermentor, and inoculating with the *L. intermedius* NRRL B-30560. Initial levels of carbon substrate should exceed 50 g/L, and preferably be at least about 100 g/L, or even in excess of 200-300 g/L. The fermentation is carried out either aerobically or anaerobically under conditions conducive to the growth of *L. intermedius* B-30560 and production of mannitol dehydrogenase. Fermentation temperature should be maintained within the range of at least about 25° C., and less than about 50° C. Preferably, the temperature is at least about 30° C. and less than or equal to about 37° C. The pH of the medium at the commencement of the fermentation is typically within the range of about 6-7, and then is controlled by addition of base at approximately pH 4.5-6.0 as the fermentation progresses. Peak mannitol levels occur shortly after the organism completes its log phase growth, typically within about 24-96 hours post-inoculation. At higher levels of initial carbon substrate, longer periods of fermentation are of course required to maximize mannitol production. In pH-controlled, fed-batch fermentations, initial levels of carbon substrate may be lower than described above, and then supplemented as the fermentation progresses. With corn steep liquor replacing peptone and yeast extract, longer periods of fermentation are required to maximize mannitol production.

Upon completion of the fermentation, mannitol may be recovered from the culture using techniques conventional in the art. For example, when mannitol is present in the culture broth at levels exceeding the solubility limit (180 g/L at 25° C.), it can be recovered from solution by cooling crystallization. In practice, mannitol would be crystallized from the crude fermentation broth by chilling the crude broth to about 4° C. After mannitol recovery, lactic acid and acetic acid can be easily recovered from the fermentation broth by electrodialysis.

Mannitol dehydrogenase, the enzyme responsible for mannitol production in the aforementioned fermentation, can be isolated from the cells by breaking the cells with glass beads.

While not desiring to be bound to any particular theory of operation, it appears that mannitol produced by *L. intermedius* NRRL B-30560 is derived from the hexose phosphate pathway like other mannitol producing bacteria such as *Lac-* tobacillus sp. Y-107, *Leuconostoc* sp. Y-002 and *Leucononostoc mesenteroides*(Yun et al., 1996, supra; Yun et al., 1998, supra; Soetaert et al., 1995, supra). The process makes use of the capability of *L. intermedius* NRRL B-30560 to utilize fructose as an alternative electron acceptor, thereby reducing it to mannitol with the enzyme mannitol dehydrogenase. In this process, the reducing equivalents are generated by conversion of about one-third fructose to lactic acid and acetic acid. It is thought that enzyme reaction proceeds according to the following (theoretical) equation:

$$3 Fructose \rightarrow 2 Mannitol + Lactic\ acid + Acetic\ acid + CO_2$$

For fructose and glucose (2:1) co-fermentation, the equation becomes:

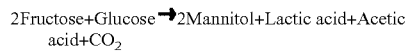
$$2 Fructose + Glucose \rightarrow 2 Mannitol + Lactic\ acid + Acetic\ acid + CO_2$$

The following examples are intended to further illustrate the invention, without any intent for the invention to be limited to the specific embodiments described therein.

Example 1

Screening of Bacterial Strains

Selection of Strains.

Seventy two bacterial strains were obtained from the ARS Culture Collection, National Center for Agricultural Utilization Research, Peoria, Ill. These strains were (with NRRL numbers): *Lactobacillus acidophilus* B-4495, *L. amylophilus* B-4436, *L. amylovorus* B-4545, *L. animalis* B14177, *L. arabinosus* B-787, *L. brevis* B-1836, *L. buchneri* B-1860, *L. bulgaricus* B-548, *L. casei* B-1922, *L. cellobiosus* B-1840, *L. coryniformis* B-4391, *L. delbrueckii* B-763, *L. fermentum* B-1915, *L. fructivorans* B-4000, *L. gasseri* B-14168, *L. gramminis* B-14857, *L. helveticus* B-1935, *L. intermedius* B-3693, *L. jensenii* B-4550, *L. leichmanii* B-4525, *L. mali* B-4565, *L. paracasei* B-4564, *L. pentosus* B-473, *L. plantarum* B-4496, *L. reuteri* B-14172, *L. rhamnosus* B-442, *L. salivarius* B-1949, *Leuconostoc amelibiosum* B-742, *L. citrovorum* B-1147, *L. mesenteroides* subsp. *dextranicum* B-1120, *L. mesenteroides* subsp. *mesenteroides* B-1209, *L. paramesenteroides* B-3471, *L. oenos* B-3474, *L. lactis* B-3468, *Pediococcus acidilactici* B-1153, *P. pentosaceus* B-14009, *Lactococcus lactis* B-1821, *Streptococcus dysgalactiae* B-688, *Enterococcus faecalis* B-537, *E. faecium* B-1295, *E. casseliflavus* B-3502, *E. hirae* B-14926, *Bacillus subtilis* NRS-744, *B. cereus* B-3711, *B. licheniformis* NRS-1264, *B. megaterium* B-14308, *B. pumilus* B-14292, *B. coagulans* NRS-609, *B. smithii* NRS-173, *B. amyloliquefaciens* B-14394, *B. mycoides* NRS-273, *Paenibacillus polymyxa* B-367, *P. peoriae* B-14750, *P. amylolyticus* B-377, *P. illinoisensis* NRS-1356, *P. chondroitinus* B-14420, *P. alginolyticus* NRS-1347, *P. pulvifaciens* B-14166, *P. lautus* NRS-666, *P. validus* NRS-1000, *P. pabuli* B-14213, *P. thiaminolyticus* B-14605, *P. macerans* B-172, *P. glucanolyticus* B-14680, *P. curdlanolyticus* B-23243, *P. apiarius* NRS-1438, *Micrococcus luteus* B-287, *M. kristinae* B-14845, *Brevibacillus brevis* NRS-604, *B. agri* B-1158, *B. choshinensis* B-23247 and *B. reuszeri* NRS-1206.

Screening Medium and Culture Conditions.

The bacterial strains listed above were evaluated for cell growth, residual substrate and product yield. The strains were cultivated on a screening medium designated as enriched MRS contained 10 g peptone, 10 g beef extract, 5 g yeast extract, 1.0 ml Tween 80, 2 g ammonium citrate, 5 g sodium acetate, 0.1 g magnesium sulfate, 0.05 g manganese sulfate and 2 g disodium phosphate per liter (final pH 6.5). The medium and the substrate (glucose or fructose 5%, w/v) were sterilized separately at 121° C. for 15 min. A 125-ml Erlenmeyer flask containing 50 ml MRS medium with substrate was inoculated with a loopful of cells taken from a stock slant and incubated at 30° C. on a rotary shaker (130 rpm). Samples were periodically withdrawn for evaluation.

Strains producing mannitol from fructose were: *L. brevis* B-1836, *L. buchneri* B-1860, *L. cellobiosus* B-1840, *L. fermentum* B-1915, *L. intermedius* B-3693 (NRRL B-30560), *Leuconostoc amelibiosum* B-742, *L. citrovorum* B-1147, *L. mesenteroides* subsp. *dextranicum* B-1120, and *L. paramesenteroides* B-3471. In addition, all these strains produced lactic acid and acetic acid. Among these nine strains, *L. intermedius* NRRL B-30560 produced mannitol at a higher rate than the other strains.

Example 2

Mannitol Production at Four Fructose Concentrations

Fermentation Experiment Protocol.

Fermentation experiments were carried out with *L. intermedius* NRRL B-30560 in simplified MRS medium (without beef extract and Tween 80). For seed culture, a 250 ml Erlenmeyer flask containing 50 ml of the medium with fructose (2%, w/v) was inoculated with a loopful of cells taken from a stock slant and incubated at 30° C. on a rotary shaker (130 rpm) for 24 h.

Batch culture experiments were performed in pH-controlled 500 ml fleakers with an initial medium volume of 300 ml at either 30° C. or 37° C. essentially as described by Bothast et al. [*Biotechnol. Lett.* 16:401-406. (1994)]. The pH was maintained at 5.0 by adding 2-8 N NaOH. Cultures were stirred magnetically using 1.5 inch stir-bars, at 130 rev/min. Samples were withdrawn periodically to determine cell growth, sugar utilization and production yield.

Effect of Fructose Concentration.

Batch cultures were conducted at four concentrations of fructose substrate: 150, 200, 250, and 300 g/L. Cell growth was monitored by measuring optical density of the appropriately diluted culture broth at 660 nm. Sugar utilization and product analysis were performed by high performance liquid chromatography (HPLC). The bacterium *L. intermedius* NRRL B-30560 produced mannitol, lactic acid and acetic acid when grown on fructose in pH-controlled fermentation (Table I). The mannitol yields were 107.6±0.5, 138.6±6.9, 175.6±5.9 and 198.3±11.0 g/L at 150, 200, 250, and 300 g/L fructose, respectively. A typical time course of fructose utilization and mannitol, lactic acid and acetic acid production at 150 g/L substrate concentration is shown in FIG. 1. The time of maximum mannitol yield varied greatly from 20 h at 150 g/L fructose to 136 h at 300 g/L fructose concentration. Also, there was a long lag period of about 72 h in growth and fructose utilization at 300 g/L fructose concentration in comparison to the lag period of about 16 h at 250 g/L fructose. However, the product patterns and yields were not much dependent on fructose concentration. The bacterium transformed fructose to mannitol from the early growth stage and it did not consume mannitol even when all supplied fructose was utilized. Moreover, the product (mannitol, lactic acid and acetic acid) concentration continued to increase slightly upon further continuation of the fermentation in most cases. The maximum cell growth ($A_{660}$ of 9.6±0.8 in 16 h) was obtained at fructose concentration of 150 g/L. The average maximum cell densities ($A_{660}$) were 4.7±0.4 in 24 h, 5.3±1.0 in 64 h and 6.5±0.8 in 136 h at fructose concentrations of 200, 250 and 300 g/L, respectively.

Small white needle-like crystals of mannitol appeared upon keeping the cell-free fermentation broth of 300 g/L fructose at 4° C. This suggests an efficient product recovery scheme for mannitol.

Example 3

Mannitol Production on Fructose and Secondary Substrate

The procedure of Example 2 was repeated, except that one third of fructose was replaced with other substrates including glucose, maltose, starch plus glucoamylase (simultaneous saccharification and fermentation, SSF), mannose, galactose, xylose, arabinose, cellobiose, raffinose and glycerol. In a separate run, two-thirds of fructose was also replaced by sucrose. The results of mannitol production by *L. intermedius* NRRL B-30560 in the two-substrate system is presented in Table II.

Figure 2:
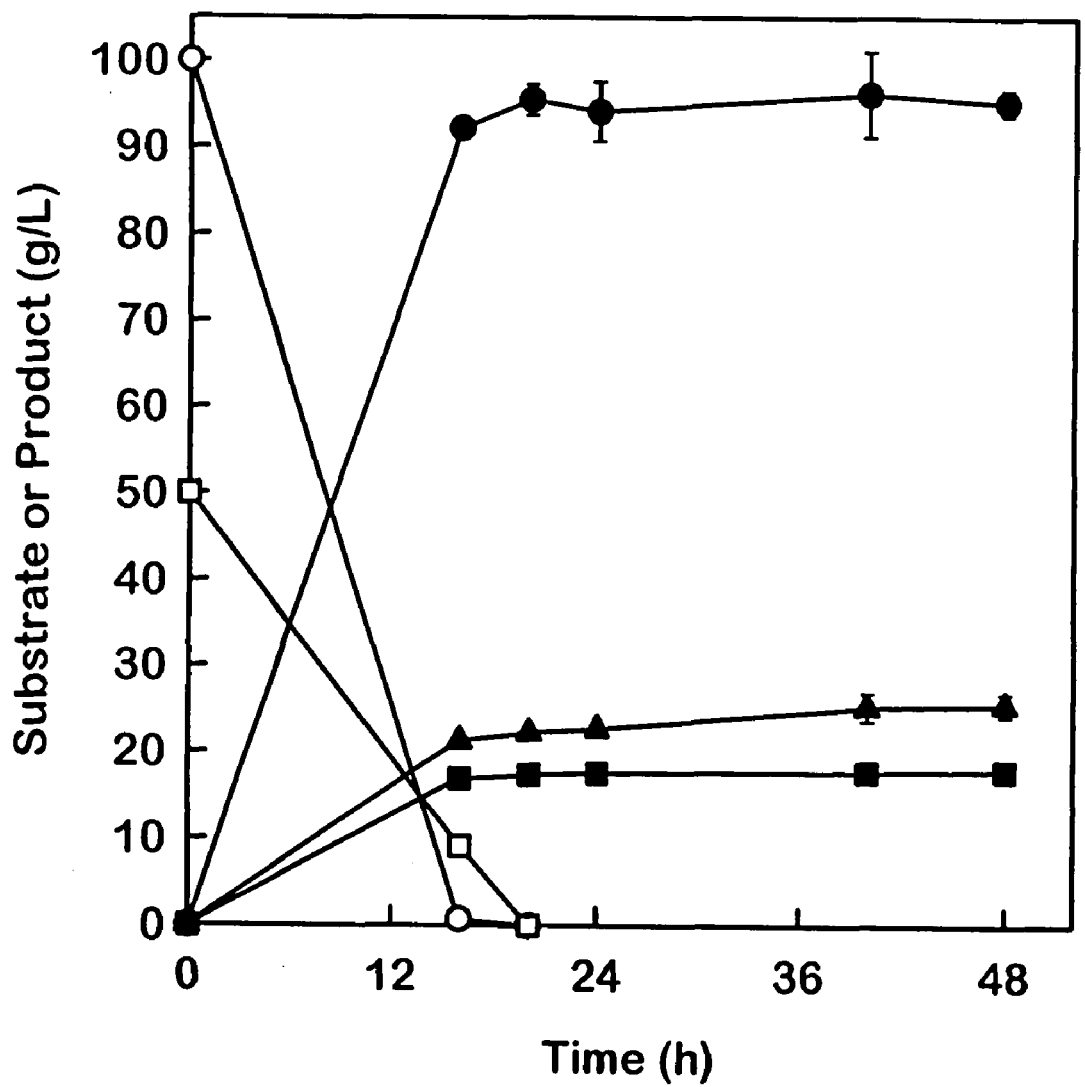
FIG. 2 is a time course of fructose (100 g/L) and glucose (50 g/L) co-utilization and mannitol production by *Lactobacillus intermedius* NRRL B-30560 in a pH-controlled batch fermentation at 37° C. Symbols: ○, Fructose; □, glucose; ●, Mannitol; ▲ Lactic acid; ■, Acetic acid.

It is clear that one-third of fructose can be replaced with glucose, starch with glucoamylase, maltose, mannose, raffinose and galactose. Two-thirds of fructose can also be replaced by sucrose. Even though arabinose was co-utilized with fructose, it did not contribute to mannitol production. The arabinose-fructose co-substrate also led to a considerable increase in the production of lactic acid and acetic acid. The bacterium was not able to co-utilize lactose, glycerol, cellobiose and xylose with fructose. A time course of fructose (100 g/L) and glucose (50 g/L) co-fermentation is shown in FIG. 2. *L. intermedius* NRRL B-30560 co-utilized fructose and glucose simultaneously and produced very similar quantities of mannitol, lactic acid and acetic acid in comparison with fructose only. The conversion efficiency of fructose to mannitol was 96%. The glucose was converted to lactic acid and acetic acid which were partially neutralized during fermentation by adding NaOH to control the pH at 5.0.

Example 4

Mannitol Production in Fed-Batch Fermentation

Figure 3:
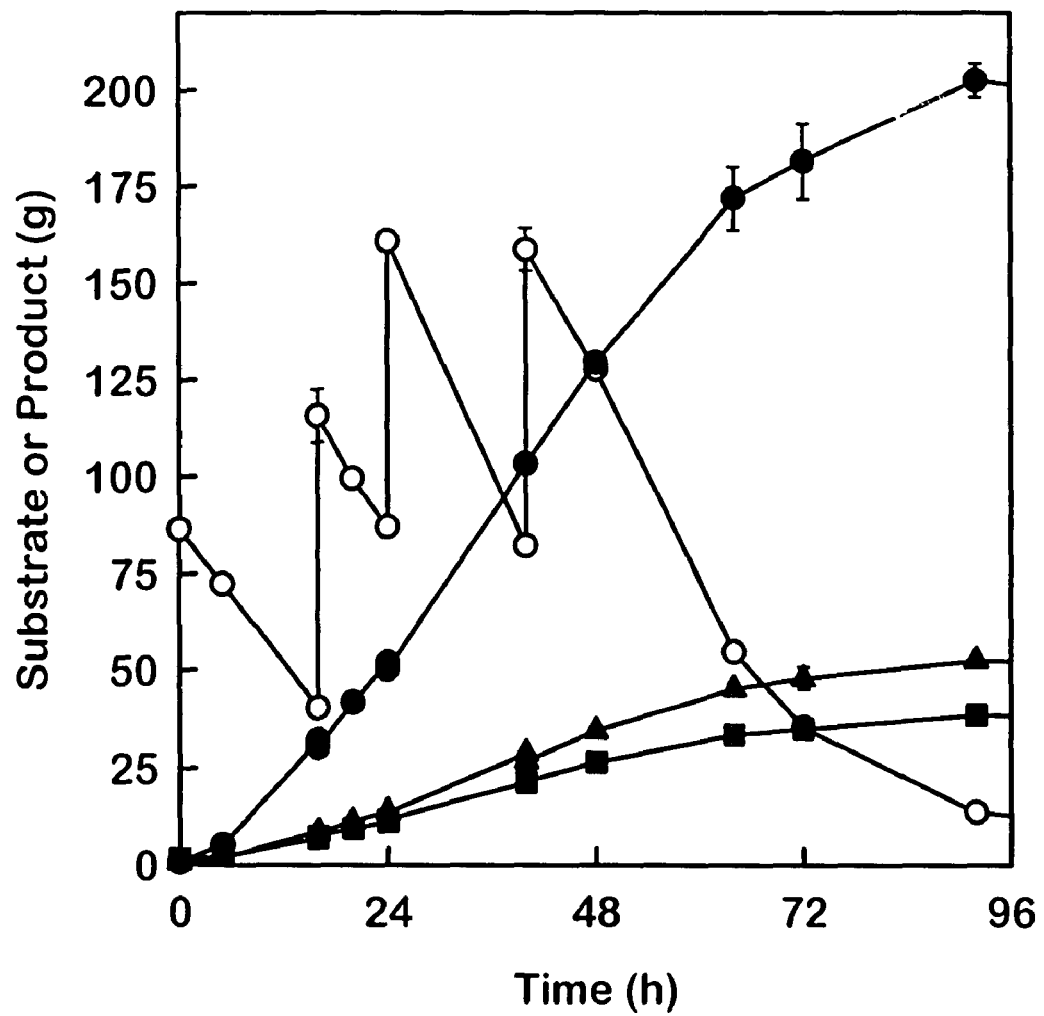
FIG. 3 are time courses of fructose utilization and mannitol production by *Lactobacillus intermedius* NRRL B-30560 in pH-controlled fed-batch fermentation at 37° C. Fructose used: 300 g/L (final concentration). Symbols: ○, Fructose; ●, Mannitol; ▲ Lactic acid; ■, Acetic acid.

In order to decrease the fermentation time required to complete 300 g/L fructose utilization as reported in Example 2, fed-batch culture technique was used. The results of fed-batch culture with *L. intermedius* NRRL B-30560 and 300 g/L fructose is shown in FIG. 3. The fermentation time decreased considerably from 136 h to 92 h by feeding equal amounts of substrate and medium four times. The yields of mannitol, lactic acid and acetic acid were 202.5±4.3, 52.6±1.0 and 38.5±0.7 g/t, respectively. The maximum cell growth (cell density, $A_{660}$ of 6.9±0.2) occurred in 64 h. The yields of mannitol, lactic acid and acetic acid from co-fermentation of fructose and glucose (2:1) at 300 g/L total substrate concentration in fed-batch fermentation were 179.4±9.3, 44.08±0.4 and 33.4±0.6 g, respectively in 160 h. The maximum cell growth ($A_{660}$ of 3.1±0.3) was observed at 88 h.

Example 5

Production of Mannitol Under Anaerobic Conditions

*L. intermedius* NRRL B-30560 was grown essentially as described in Example 2 in simplified MRS medium under anaerobic conditions using 2% fructose as the carbon source. The product patterns were analyzed by HPLC. The bacterium produced mannitol, lactic acid and acetic acid in product ratios similar to those obtained under aerobic conditions.

Example 6

Comparative Microbiological Production of Mannitol

A comparative study of mannitol production by *L. intermedius* NRRL B-30560 with those of the earlier workers is presented in Table III. Fermentations were conducted as described in Example 2, except that the other bacteria reported in Table III were grown on enriched MRS medium (including beef extract and Tween) as described in Example 1. It is expected that the reported fermentation time for *L. intermedius* NRRL B-30560 could be shortened by using the enriched MRS medium.

Example 7

Isolation of Mannitol Dehydrogenase from *L. intermedius* B-30560

The bacterium was grown in 1 L fleakers with a working volume of 700 ml at 37° C. and initial pH of 6.5 for 16 h using 15% fructose at which time mannitol dehydrogenase activity reached a maximum. The pH was controlled at 5.0 with 5 M NaOH. The cells were separated from the fermentation broth by centrifugation (15,000 g, 25 min) and washed with 50 mM phosphate buffer, pH 5.5. The washed cells were then suspended in the same buffer plus 1 mM Dithiothreitol (DTT) and treated with glass beads overnight. After centrifugation (30,000 g, 20 min), the clear supernatant was used as crude mannitol dehydrogenase (MDH) preparation. The enzyme was then subjected to DEAE-BioGel A column chromatography, BioGel A gel filtration, octyl-Sepharose column chromatography and finally Bio Gel HT column chromatography. The isolated mannitol dehydrogenase showed homogeneity as judged by native SDS-PAGE, SDS-PAGE and isoelectric gel electrophoresis. The first 20 N-terminal amino acids of purified mannitol dehydrogenase from L. intermedius B-30560 are Met-Lys-Ala-Leu-Val-Leu-Gln-Gly-Ile-Lys-Asp-Leu-Ala-Val-Gln-Asp-Tyr-Glu-Val-Pro (SEQ ID NO: 1). The purified enzyme was used for conversion of fructose to mannitol (see Example 8).

Example 8

Biochemical Production of Mannitol

In a reaction mixture containing 1.4% fructose, 50 mM phosphate buffer, pH 5.0 and 0.2 mM NADPH or NADH, the purified enzyme obtained in Example 7 was fairly active over a pH range 4.5-8.5 and temperature up to 50° C. with optimum pH being 5.5 and optimum temperature at 35° C. The enzyme converted fructose to mannitol almost quantitatively within 6 h at pH 5.0 and 30° C. The enzyme did not show any activity towards conversion of xylose to xylitol and arabinose to arabitol.

TABLE I

Mannitol production from fructose by L. intermedius NRRL B-30560 in pH controlled batch fermentation.[a]

| Fructose (g/L) | Time (h) | Mannitol (g/g) | Lactic acid (g/g) | Acetic acid (g/g) |
|---|---|---|---|---|
| 150 | 20 | 0.72 ± 0.00 | 0.17 ± 0.00 | 0.12 ± 0.00 |
| 200 | 40 | 0.69 ± 0.03 | 0.17 ± 0.00 | 0.13 ± 0.00 |
| 250 | 64 | 0.70 ± 0.02 | 0.16 ± 0.00 | 0.12 ± 0.00 |
| 300 | 136 | 0.66 ± 0.03 | 0.15 ± 0.01 | 0.11 ± 0.00 |

[a]At 37° C., 130 rpm, Initial pH 6.5, pH controlled at 5.0, 500 ml fleaker with 300 ml medium.

TABLE II

Mannitol production using two substrate system (fructose and another sugar) by Lactobacillus intermedius NRRL B-30560 in pH-controlled batch fermentation.[a]

| Substrate (g/L) | Time (h) | Mannitol (g/L) | Lactic acid (g/L) | Acetic acid (g/L) |
|---|---|---|---|---|
| Fructose (100) plus glucose (50) | 20 | 97.3 ± 2.6 | 23.2 ± 0.5 | 15.8 ± 0.4 |
| Fructose (50) plus sucrose (100) | 64 | 84.5 ± 0.7 | 23.6 ± 1.6 | 13.6 ± 0.3 |
| Fructose (100) plus starch (50) and glucoamylase | 24 | 86.6 ± 1.2 | 25.7 ± 0.5 | 13.8 ± 0.1 |
| Fructose (100) Plus maltose (50) | 15 | 95.9 ± 0.8 | 20.9 ± 0.2 | 14.2 ± 0.4 |
| Fructose (100) plus mannose (50) | 89 | 89.1 ± 1.9 | 18.4 ± 2.6 | 14.6 ± 1.9 |
| Fructose (100) plus galactose (50) | 15 | 82.3 ± 0.7 | 16.7 ± 0.7 | 13.2 ± 0.2 |
| Fructose (100) plus raffinose (50) | 40 | 94.1 ± 0.7 | 24.8 ± 0.3 | 15.3 ± 0.1 |
| Fructose (100) plus arabinose (50) | 64 | 61.6 ± 0.9 | 41.1 ± 1.1 | 27.3 ± 1.2 |

[a]At 37° C., except for starch at 30° C., initial pH 6.5, pH maintained at 5.0, 130 rpm, 500 ml fleaker with 300 ml medium.

TABLE III

Comparison of mannitol production by L. intermedius B-30560 with those of earlier workers

| Microorganism | Substrate (g/L) | Time[a] (h) | Yield[b] (%) | Reference |
|---|---|---|---|---|
| Bacteria | | | | |
| Lactobacillus intermedius B-30560 | Fructose (150) | 15 | 72 | This work |
| | Fructose (200) | 40 | 69 | This work |
| | Fructose (250) | 64 | 70 | This work |
| | Fructose (300) | 136 | 66 | This work |
| | Fructose (300) | 926 | 67 | This work (fed-batch) |
| | Fructose (100) + Glucose (50) | 20 | 65 | This work |
| Lactobacillus sp. B001 | Fructose (100) + Glucose (50) | 24 | 65 | Itoh et al., 1991, supra |
| Lactobacillus sp. Y-107 | Fructose (100) | 120 | 73 | Yun et al., 1998, supra |
| Lactobacillus sanfranciscensis | Fructose (?) | 120 | 60 g/L | Korakli et al., 2000, supra |
| Leuconostoc mesenteroides | Fructose (100) + Glucose (50) | 35 | 60 | Soetart et al., 1995, supra |
| L. mesenteroides | Fructose (08) | — | 30-40 | Erten, 1998, Proc. Biochem 33: 735-739 |
| Leuconostoc sp. Y-002 | Fructose (50) | 25 | 40 | Yun et al., 1998, supra |
| Yeast | | | | |
| Candida magnoliae | Fructose (150) | 168 | 45 | Song et al., 2002 Biotechnol. Lett. 24: 9-12 |
| Torulopsis versalitis | Glucose (194) | 240 | 28 | Onishi et al., 1968 Appl. Microbiol. 16: 1847-1852 |
| Torulopsis mannitofaciens | Glycerol (100) | 168 | 31 | Onishi et al., 1970 Biotechnol. Bioeng. 12: 913-920 |
| Fungi | | | | |
| Aspergillus candidus | Glucose (32) | 288 | 69 | Smiley et al., 1967 Biotechnol. Bioeng. 9: 365-374 |
| Candida zeylannoides | n-Paraffin (100) | 100 | 52 | Hattori et al., 1974 Agri. Biol. Chem. 38: 1203-1208 |
| Penicillium scabrosum | Sucrose (150) | 288 | 40 | Hendriksen et al., 1988, J. Chem. Techno. Biotechnol. 43: 223-228 |

[a]Time to reach maximum mannitol yield.
[b]Mannitol yields were calculated on the basis of initial sugars employed.

I claim:

1. Substantially pure mannitol dehydrogenase isolated from *Lactobacillus intermedius* NRRL B-30560.

* * * * *